US012589260B2

(12) United States Patent
Knox et al.

(10) Patent No.: US 12,589,260 B2
(45) Date of Patent: Mar. 31, 2026

(54) TIMING-BASED METHODS, SYSTEMS, AND COMPUTER READABLE MEDIUMS FOR A GATED LINEAR ACCELERATOR

(71) Applicant: Elekta Limited, Crawley (GB)

(72) Inventors: Christopher Knox, Crawley (GB);
Joshua Freedman, Crawley (GB);
Kevin John Brown, Crawley (GB);
David Roberts, Crawley (GB)

(73) Assignee: Elekta Limited, Crawley (GB)

( * ) Notice: Subject to any disclaimer, the term of this patent is extended or adjusted under 35 U.S.C. 154(b) by 156 days.

(21) Appl. No.: 18/477,115

(22) Filed: Sep. 28, 2023

(65) Prior Publication Data

US 2024/0100364 A1     Mar. 28, 2024

(30) Foreign Application Priority Data

Sep. 28, 2022    (GB) ..................................... 2214184

(51) Int. Cl.
*A61N 5/10* (2006.01)
*G06F 1/12* (2006.01)
*G16H 40/63* (2018.01)

(52) U.S. Cl.
CPC ......... *A61N 5/1068* (2013.01); *A61N 5/1077* (2013.01); *G06F 1/12* (2013.01); *G16H 40/63* (2018.01); *A61N 2005/1055* (2013.01); *A61N 2005/1074* (2013.01)

(58) Field of Classification Search
None
See application file for complete search history.

(56) References Cited

U.S. PATENT DOCUMENTS

| | | | |
|---|---|---|---|
| 2009/0093705 A1* | 4/2009 | Vangdal | G01R 33/283 |
| | | | 600/410 |
| 2021/0225501 A1 | 7/2021 | Aguilar et al. | |
| 2023/0125842 A1* | 4/2023 | Dempsey | G01R 33/50 |
| | | | 600/411 |
| 2024/0325088 A1* | 10/2024 | Paulson | A61N 5/1049 |

FOREIGN PATENT DOCUMENTS

| | | |
|---|---|---|
| CN | 115664575 A | 1/2023 |
| EP | 3805773 A1 | 4/2021 |
| WO | 2023067528 | 4/2023 |

OTHER PUBLICATIONS

"European Application Serial No. 23199721.4, European Search Report dated Feb. 16, 2024", (Feb. 16, 2024), 9 pgs.
Borman, P. T. S., "Characterization of imaging latency for real-time MRI-guided radiotherapy", Physics in Medicine and Biology 63.15, (2018), 155023.

(Continued)

*Primary Examiner* — Hoon K Song
(74) *Attorney, Agent, or Firm* — Schwegman Lundberg & Woessner, P.A.

(57) ABSTRACT

Timing-based methods, systems, and computer readable mediums for a gated linear accelerator include synchronising a local clock of the linear accelerator with a clock of a patient monitoring system, determining latencies within one or more MR-gated radiotherapy processes and implementing latency based interlocks.

20 Claims, 6 Drawing Sheets

(56)          References Cited

OTHER PUBLICATIONS

Hu, Panpan, "Dosimetry impact of gating latency in cine magnetic resonance image guided breath-hold pancreatic cancer radiotherapy", Physics in Medicine and Biology 67.5, (2022), 055008.

Kim, Taeho, "Clinical experience of MRI4D QUASAR motion phantom for latency measurements in 0.35 T MR-LINAC", Journal of applied clinical medical physics 22.1, (2021), 128-136.

"British Application Serial No. 2214184.0, Examination Report dated Feb. 1, 2024", (Feb. 1, 2024), 2 pgs.

"United Kingdom Application Serial No. 2214184.0, Examination Report dated Mar. 14, 2023", (Mar. 14, 2023), 6 pgs.

"European Application No. 23 199 721.4, Office Action dated Feb. 6, 2026", Feb. 6, 2026, 5 pgs.

* cited by examiner

TIMING-BASED METHODS, SYSTEMS, AND COMPUTER READABLE MEDIUMS FOR A GATED LINEAR ACCELERATOR

CLAIM FOR PRIORITY

This application claims the benefit of priority of British Application Serial No. 2214184.0, filed Sep. 28, 2022, which is hereby incorporated by reference in its entirety.

TECHNICAL FIELD

This disclosure relates to methods, systems, and computer readable mediums for performing synchronizing and implementing interlocks in a gated radiotherapy device.

BACKGROUND

The present disclosure relates to a control system of a machine, apparatus or device for radiotherapy, and a method implemented therein. Radiotherapy devices are an important tool in modern cancer treatment. The device may be suitable for delivering a beam of radiation to a patient in order to treat a tumour. An example of a radiation source for producing a beam is a linear accelerator (linac). Clinical linac devices are configured to deliver high energy radiation to a patient.

To effectively deliver radiation to a tumour, the radiation beam produced by the linac is targeted at the tumour. As one example, an MR-linac (magnetic resonance linear accelerator), such as the Elekta-Unity MR-linac, uses registration to an MR image of a patient located with a field of delivery of the linac to target its radiation beam at a tumour. As the duration of radiotherapy delivery within a given treatment session is generally greater than the amount time that a patient can hold their breath for, the radiotherapy is gated to the patient's respiratory cycle so that the radiation beam is only delivered to the patient during a portion of the patient's respiratory cycle that corresponds to their tumour being correctly targeted. Multiple options are available for performing respiratory gating, including the use of: respiratory bellows, a 1D navigator signal through the patient's diaphragm whilst they are located within the field of deliver of the linac, and a 2D or 3D MR image of the patient whilst they are located within the field of deliver of the linac.

It is important to make sure that both a sufficient dose of radiation is delivered to the patient's tumour and that irradiation of healthy parts of the patient is minimised and so good quality gating decisions are required. Moreover, it is important to take action to prevent errors in the gating processes from resulting in erroneous irradiation of the patient.

BRIEF DESCRIPTION OF THE FIGURES

Specific embodiments are now described, by way of example only, with reference to the drawings, in which.

DETAILED DESCRIPTION

MR-Dated Radiotherapy

Figure 1:
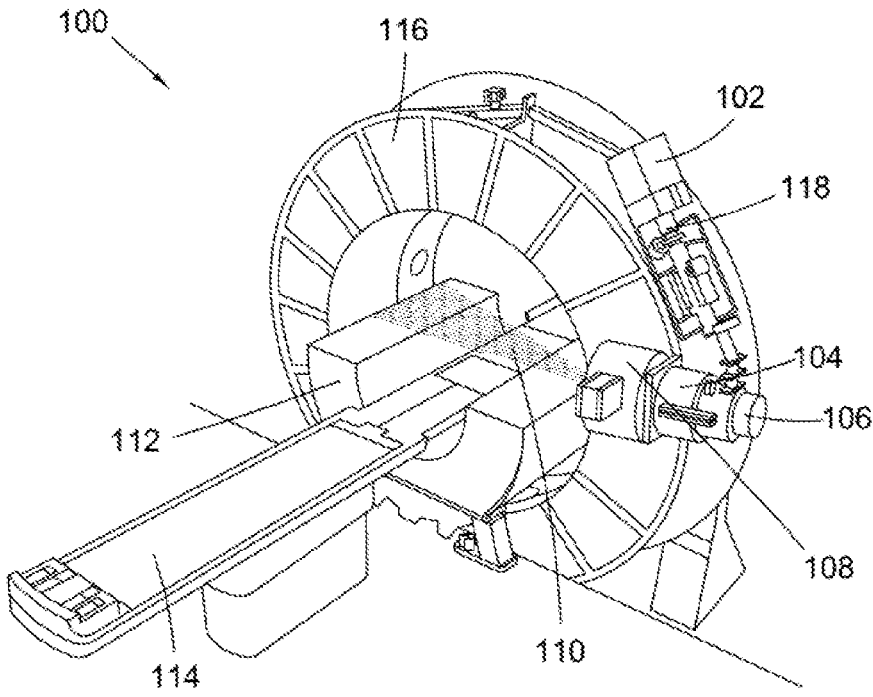
FIG. 1 shows a radiotherapy device or apparatus according to the present disclosure.

FIG. 1 depicts a radiotherapy device suitable for delivering, and configured to deliver, a beam of radiation to a patient during radiotherapy treatment. The device and its constituent components will be described generally for the purpose of providing useful accompanying information for the present invention. The device depicted in FIG. 1 is in accordance with the present disclosure and is suitable for use with the disclosed systems and apparatuses. While the device in FIG. 1 is an MR-linac, the implementations of the present disclosure may be any radiotherapy device, for example a linac device.

The device 100 depicted in FIG. 1 is an MR-linac. The device 100 comprises both MR imaging apparatus 112 and radiotherapy (RT) apparatus which may comprise a linac device. The MR imaging apparatus 112 is shown in cross-section in the diagram. In operation, the MR scanner produces MR images of the patient, and the linac device produces and shapes a beam of radiation and directs it toward a target region within a patient's body in accordance with a radiotherapy treatment plan. The depicted device does not have the usual 'housing' which would cover the MR imaging apparatus 112 and RT apparatus in a commercial setting such as a hospital.

The MR-linac device depicted in FIG. 1 comprises a source of radiofrequency waves 102, a waveguide 104, a source of electrons 106, a source of radiation 106, a collimator 108 such as a multi-leaf collimator configured to collimate and shape the beam, MR imaging apparatus 112, and a patient support surface 114. In use, the device would also comprise a housing (not shown) which, together with the ring-shaped gantry, defines a bore. The moveable support surface 114 can be used to move a patient, or other subject, into the bore when an MR scan and/or when radiotherapy is to commence. The MR imaging apparatus 112, RT apparatus, and a subject support surface actuator are communicatively coupled to a controller or processor. The controller is also communicatively coupled to a memory device comprising computer-executable instructions which may be executed by the controller. As used herein, a controller may also be referred to as a control device.

The RT apparatus comprises a source of radiation and a radiation detector (not shown). Typically, the radiation detector is positioned diametrically opposed to the radiation source. The radiation detector is suitable for, and configured to, produce radiation intensity data. In particular, the radiation detector is positioned and configured to detect the intensity of radiation which has passed through the subject. The radiation detector may also be described as radiation detecting means, and may form part of a portal imaging system.

The radiation source may comprise a beam generation system. For a linac, the beam generation system may comprise a source of RF energy 102, an electron gun 106, and a waveguide 104. The radiation source is attached to the rotatable gantry 116 so as to rotate with the gantry 116. In this way, the radiation source is rotatable around the patient so that the treatment beam 110 can be applied from different angles around the gantry 116 to a field of delivery of the linac. In a preferred implementation, the gantry is continuously rotatable. In other words, the gantry can be rotated by 360 degrees around the patient, and in fact can continue to be rotated past 360 degrees. The gantry may be ring-shaped. In other words, the gantry may be a ring-gantry.

The source 102 of radiofrequency waves, such as a magnetron, is configured to produce radiofrequency waves. The source 102 of radiofrequency waves is coupled to the waveguide 104 via circulator 118, and is configured to pulse radiofrequency waves into the waveguide 104. Radiofrequency waves may pass from the source 102 of radiofrequency waves through an RF input window and into an RF input connecting pipe or tube. A source of electrons 106, such as an electron gun, is also coupled to the waveguide 104 and is configured to inject electrons into the waveguide 104. In the electron gun 106, electrons are thermionically emitted from a cathode filament as the filament is heated. The temperature of the filament controls the number of electrons injected. The injection of electrons into the waveguide 104 is synchronized with the pumping of the radiofrequency waves into the waveguide 104. The design and operation of the radiofrequency wave source 102, electron source and the waveguide 104 is such that the radiofrequency waves accelerate the electrons to very high energies as the electrons propagate through the waveguide 104.

The design of the waveguide 104 depends on whether the linac accelerates the electrons using a standing wave or travelling wave, though the waveguide typically comprises a series of cells or cavities, each cavity connected by a hole or 'iris' through which the electron beam may pass. The cavities are coupled in order that a suitable electric field pattern is produced which accelerates electrons propagating through the waveguide 104. As the electrons are accelerated in the waveguide 104, the electron beam path is controlled by a suitable arrangement of steering magnets, or steering coils, which surround the waveguide 104. The arrangement of steering magnets may comprise, for example, two sets of quadrupole magnets.

Once the electrons have been accelerated, they may pass into a flight tube. The flight tube may be connected to the waveguide by a connecting tube. This connecting tube or connecting structure may be called a drift tube. The electrons travel toward a heavy metal target which may comprise, for example, tungsten. Whilst the electrons travel through the flight tube, an arrangement of focusing magnets act to direct and focus the beam on the target.

To ensure that propagation of the electrons is not impeded as the electron beam travels toward the target, the waveguide 104 is evacuated using a vacuum system comprising a vacuum pump or an arrangement of vacuum pumps. The pump system is capable of producing ultra-high vacuum (UHV) conditions in the waveguide 104 and in the flight tube. The vacuum system also ensures UHV conditions in the electron gun. Electrons can be accelerated to speeds approaching the speed of light in the evacuated waveguide 104.

The source of radiation is configured to direct a beam 110 of therapeutic radiation toward a patient positioned on the patient support surface 114. The source of radiation may comprise a heavy metal target toward which the high energy electrons exiting the waveguide are directed. When the electrons strike the target, X-rays are produced in a variety of directions. A primary collimator may block X-rays travelling in certain directions and pass only forward travelling X-rays to produce a treatment beam 110. The X-rays may be filtered and may pass through one or more ion chambers for dose measuring. The beam can be shaped in various ways by beam-shaping apparatus, for example by using a multi-leaf collimator 108, before it passes into the patient as part of radiotherapy treatment.

In some implementations, the source of radiation is configured to emit either an X-ray beam or an electron particle beam. Such implementations allow the device to provide electron beam therapy, i.e. a type of external beam therapy where electrons, rather than X-rays, are directed toward the target region. It is possible to 'swap' between a first mode in which X-rays are emitted and a second mode in which electrons are emitted by adjusting the components of the linac. In essence, it is possible to swap between the first and second mode by moving the heavy metal target in or out of the electron beam path and replacing it with a so-called 'electron window'. The electron window is substantially transparent to electrons and allows electrons to exit the flight tube.

The subject or patient support surface 114 is configured to move between a first position substantially outside the bore, and a second position substantially inside the bore. In the first position, a patient or subject can mount the patient support surface. The support surface 114, and patient, can then be moved inside the bore, to the second position, in order for the patient to be imaged by the MR imaging apparatus 112 and/or imaged or treated using the RT apparatus. The movement of the patient support surface is effected and controlled by a subject support surface actuator, which may be described as an actuation mechanism. The actuation mechanism is configured to move the subject support surface in a direction parallel to, and defined by, the central axis of the bore. The terms subject and patient are used interchangeably herein such that the subject support surface can also be described as a patient support surface. The subject support surface may also be referred to as a moveable or adjustable couch or table.

The radiotherapy apparatus/device depicted in FIG. 1 also comprises MR imaging apparatus 112. The MR imaging apparatus 112 is configured to obtain images of a subject positioned, i.e. located, on the patient support surface 114. The MR imaging apparatus 112 may also be referred to as the MR imager. The MR imaging apparatus 112 may be a conventional MR imaging apparatus operating in a known manner to obtain MR data, for example MR images. The skilled person will appreciate that such a MR imaging apparatus 112 may comprise a primary magnet, one or more gradient coils, one or more receive coils, and an RF pulse applicator. The operation of the MR imaging apparatus is controlled by the controller. While the discussion herein may focus on MR imaging by way of example, alternatively or in addition to MR imaging, one or more other imaging techniques, modalities, sensors or detectors may be used, such as CT/X-ray, PET, optical imaging/cameras, infra-red imaging, ultra-sound imaging or time-of-flight techniques. Any one or more of these may be used to determine the position of the target. As used herein, references to determining the position of the target may be used interchangeably with determining the position of the subject or of a part of the subject.

The controller is a computer, processor, or other processing apparatus. The controller may be formed by several discrete processors; for example, the controller may comprise a processor for each of the various individual components of the radiotherapy device as described herein. The controller is communicatively coupled to a memory, e.g. a computer readable medium. The controller may be communicatively coupled to one, multiple or all of the various individual components of the radiotherapy device as described herein. As used herein, the controller may also be referred to as a control device and/or a control system.

The linac device also comprises several other components and systems as will be understood by the skilled person. For example, in order to ensure the linac does not leak radiation, appropriate shielding is also provided.

The radiotherapy device and/or the control device may be configured to perform any of the method steps presently disclosed and may comprise computer executable instructions which, when executed by a processor cause the processor to perform any of the method steps presently disclosed, or when executed by the control device cause the control device to perform any of the method steps presently disclosed, or when executed by the radiotherapy device cause the radiotherapy device to perform any of the method steps presently disclosed. Any of the steps that the radiotherapy device and/or the control device is configured to perform may be considered as method steps of the present disclosure and may be embodied in computer executable instructions for execution by a processor. A computer-readable medium may comprise the above-described computer executable instructions.

A position of a target within a subject may be measured, monitored or determined during a radiotherapy treatment, for example using MR imaging. As the skilled person will be familiar with, MR imaging is an imaging technique which involves placing a subject in a strong magnetic field which aligns the magnetic moments of protons in the subject to produce a net magnetization. Irradiating the subject with radiofrequency (RF) pulses of a particular resonant frequency tips the net magnetization of these protons by a flip-angle $\alpha°$ into a plane perpendicular to the strong magnetic field. After the RF pulse is completed, the tipped net magnetization of these protons realigns with the strong magnetic field. The changing magnetic flux generated during realignment induces a voltage in a coil. This is measured and analysed to provide information on the distribution of different tissues within the subject.

However, there is a time delay or latency between a target being in a particular location and action being taken based on sensing of the target being in that location. For example, for MR imaging, this latency may include contributions from the duration or frequency of acquisition, the duration of reconstruction of an image, the preparation of the image for transmission, the transmission of the image to a motion manager, the determination of a decision based on the image and reference data/pre-determined conditions, and the response time of the radiotherapy device to alter or interrupt the treatment. These contributions mean that the response to the target being in a particular location is based on the location of the target at some point in the past, i.e. in the past by a time period referred to as the system latency. If the target moves during this time period, the use of such out of date information may lead to incorrect or inaccurate or delayed responses, which can cause dosimetric errors.

Figure 2:
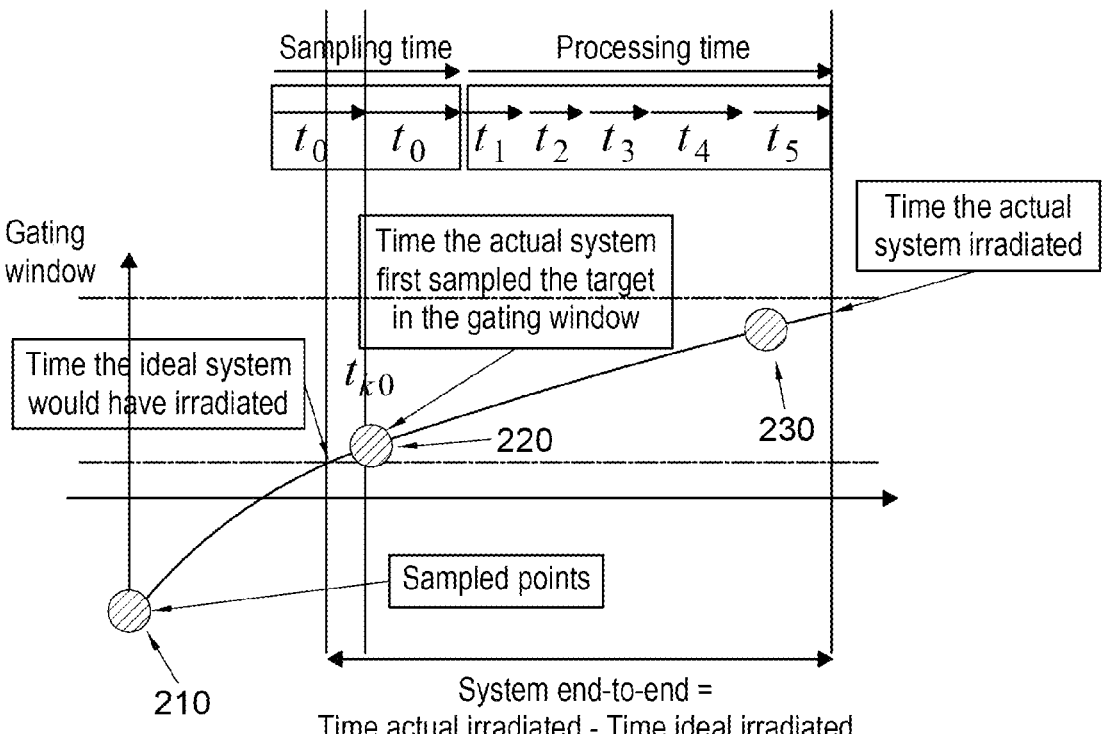
FIG. 2 is a graph showing time versus position for a free breathing patient.

FIG. 2 is a graph showing time on the x-axis versus on the y-axis position of a portion of a free breathing patient. The graph of FIG. 2 is for illustrative purposes only and the y-axis position may be conceptualised as the distance of a patient's tumour along the cyclical movement path that it will take due to the patient's respiratory motion. The dashed horizontal lines show the upper and lower limits of the y-axis position that define a gating window within which the tumour can acceptably be irradiated. At point 210, the target tumour is not yet within the gating window. The latency chain begins with the acquisition by sampling k-space for a 2D motion-management image in a period $t_{acq}=2t_0$ by an MR sub-system (hereinafter the 'MR system') of the MR-linac. As the acquisition of k-space is not instantaneous and the target tumour will experience motion during the acquisition duration, an acquisition time $t_{k0}$ (point 220 in FIG. 2) that corresponds to halfway through this acquisition is chosen as the 'representative', 'typical' or 'most likely' time to represent the target position in the image.

Once all the k-space data is acquired, the data is then processed at points ($t_{1-5}$) which respectively correspond to durations for: reconstruction of the 2D image, preparation for transmission of the image by the MR sub-system to a motion manager of the linac's control system, transmission of the image to the motion manager, making a gating decision based on the received image, and time to turn on the radiation beam (e.g. >=90% dose rate threshold). The patient is then irradiated at point 230. There is a similar chain of times associated with turning the radiation beam off. The required sampling and processing times ($t_{0-5}$) means that there is a delay (a latency) between when the system would ideally irradiate the patient and when the system actually irradiates the patient. As can be seen, not only is there a temporal (x-axis) difference between the time the ideal system would irradiate the patient and when it does, but there is also a spatial (y-axis) difference between the position that the system would irradiate the patient and where it does. When a patient is irradiated in a position other than an intended position, the above mentioned dosimetry errors can ensue.

Gating Latency Assessment

To assess latency during gated radiotherapy, patient monitoring data to be used for gating is received from a patient monitoring system by the control system along with an acquisition time of the patient monitoring data. For MR-gated radiotherapy, the patient monitoring system may be the MR system of the MR-linac, the patient monitoring data may be MR data (such as k-space data or reconstructed image data for a patient in a field of delivery (of radiation) of the linac) and the acquisition time may be a time (according to a local 'monitoring' clock of the patient monitoring system) of acquisition of a central line or portion of k-space. Other possible acquisition times for the MR data include the start and/or end time of the k-space acquisition or a reconstruction time of a received MR image.

Comparison by the control system of the received acquisition time with a time of a local 'control' clock of the control system will enable determination of a latency of the patient monitoring data. As gating decisions affecting dosimetry will be made based upon the so-determined latency, ensuring accuracy of the latency determination is important. Although one would expect computers respectively controlling an MR machine and a linac to have respective clocks that contemporaneously show the same date and pretty much the same time, it has been found that such clocks are not sufficiently synchronized to avoid causing dosimetry errors consequent to errors in measured latency. In particular, if there is an error in measured latency, respiratory motion of the patient will mean that the patient is not where the control system determines them to be—which could result in an unintended part of the patient being irradiated.

By specifically synchronizing the clock of the control system with the clock of the patient monitoring system, the acquisition time and the time of the control system are put into the same time context and the control system is thus able to accurately determine latency. Synchronization may occur by way of a Time Sync Server (not shown) of the MR-linac or may be performed between the control system and the patient monitoring system—for example directly therebetween.

The time of the control clock that is compared to the acquisition time may be: a current time, a time of receipt of patient monitoring data (such as a reconstructed MR image), a time of transmission of the patient monitoring data to a motion manager, a time of determination of a gating decision based on the patient monitoring data, a time of instruction by the control system/a beam generation subsystem thereof for the delivery of radiotherapy to the patient, a time of altering or turning the radiation beam on/off, or a time of detection of delivered radiotherapy—for example as may be seen by a dosimetry measurement solution monitoring the beam output.

Figure 3:
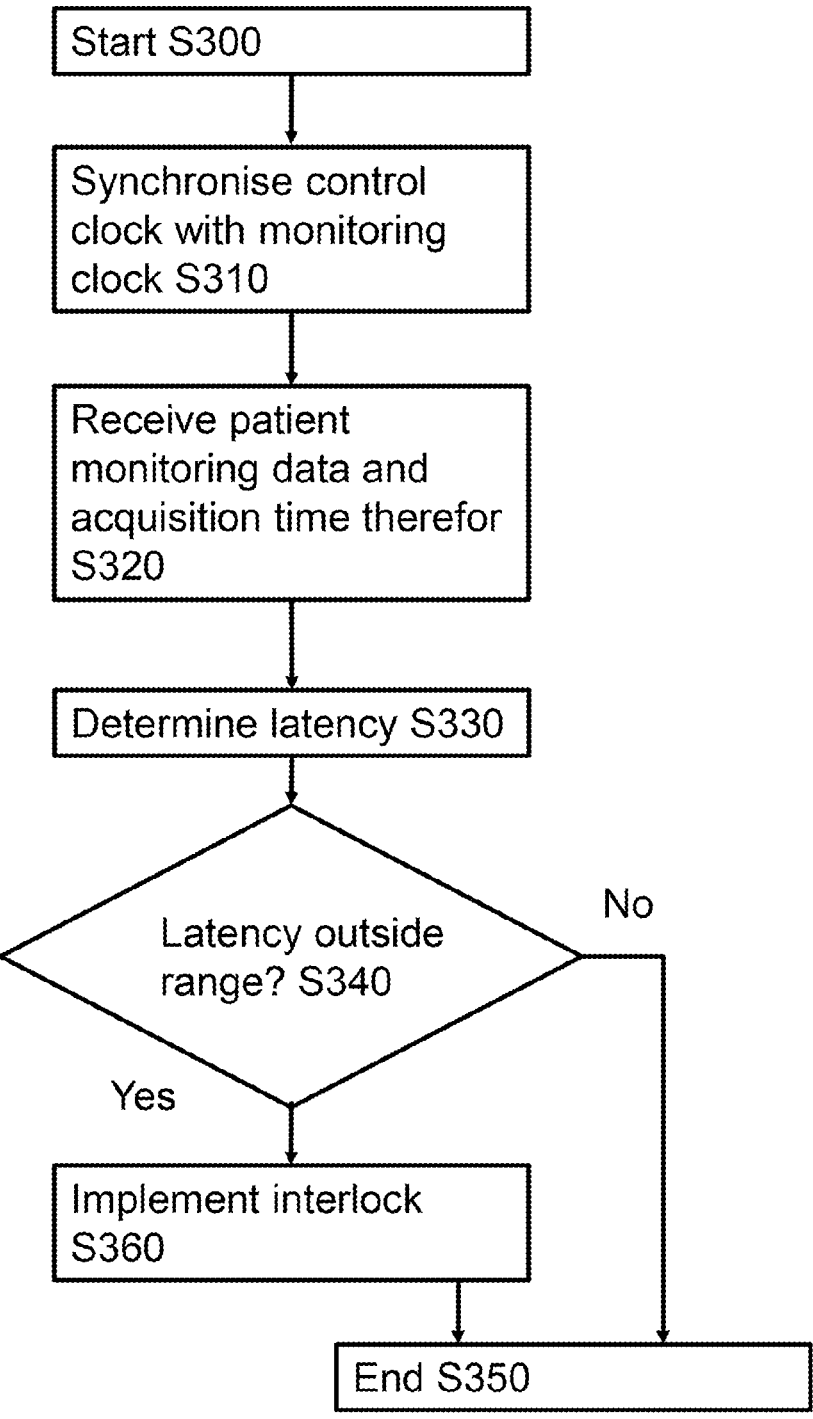
FIG. 3 is a flow diagram for a process of determining latency.

FIG. 3 is a flow diagram for a process of determining latency which starts at step S300. At step S310, a 'control' clock of a control system of an MR-linac is synchronized with a 'monitoring' clock of a patient monitoring system—in this case an MR system of the MR-linac. At step S320, patient monitoring information (in this case MR information comprising k-space data or a reconstructed MR image) is received from the patient monitoring system at the control system along with an acquisition time for that patient monitoring information. At step S330, the control system compares the acquisition time with a time of the control clock to determine a latency of the patient monitoring data. The determined latency is then assessed at step S340 to see whether it lies outside a predetermined range of acceptable latencies. The predetermined range may be bounded by a single threshold demarking latency values on one side of which lie within the predetermined range and on the other side of which do not. The threshold itself may or may not be included within the predetermined range. As one possibility, the range of acceptable latencies is determined to ensure the latency falls within a time window that corresponds to a range of positions in the patient's respiratory cycle for which the current setup of the radiation beam would result in an acceptable irradiation of the patient's tumour without unacceptable irradiation of healthy tissue.

If the latency does not lie outside the predetermined range then the method stops at step S350. If the latency lies outside the predetermined range, then at step S360 an interlock is implemented to prevent one or more actions from being taken. As one possibility, the interlock may be arranged to prevent irradiation of the patient—for example by stopping ongoing radiation or preventing an initiation of radiation. This may be achieved by disabling the electron gun 106—for example by sending a signal to cause the placement of an opaque material between the electron gun 106 and the patient or by ceasing provision of a 'fire gun' signal to the electron gun. As an additional or alternative possibility, the interlock may be arranged to prevent display on a monitor associated with the MR-linac of an image based on the patient monitoring data—such as an MR image of the patient in the field of delivery. By blocking the display of such an image when it is determined that it has an unacceptable latency, operators and clinicians are prevented from making decisions based on images that are out of date (or at least not real time representations of the patient).

Although the above has been described with reference to a method performed at a control system, it may be performed at a beam generation subsystem of the control system.

The predetermined range that latency is assessed against may vary based on the bodily location of the patient's tumour (which will have a bearing on the amount of tumour movement caused by respiration) and/or the imaging protocol used. For example, a 2D MR image with a time stamped acquisition time at the middle of its k-space acquisition and a 400 ms acquisition time will have a different end-to-end time that a 3D MR image acquired over a number of seconds.

Although the above has been described by reference to MR-gated radiotherapy, the patient monitoring system need not be an MR system and may instead be a system for imaging using another modality such as ultrasound, X-ray or CT and/or may comprise a device such as a bellows for providing a signal indicative of a current phase of a wearer's respiratory cycle, with the acquisition time of patient monitoring data acquired according to such a patient monitoring system being a time of collection thereof.

Beneficially, the above approach enables an improved assessment of latency thereby enabling better targeting of tumourous tissue and facilitating the reduction/avoidance of healthy tissue irradiation. The approach can be deployed on a real-time basis during treatment with every gating-based electron gun hold/fire instruction being checked. This would not be possible with external quality assurance equipment (which would also be invasive to a clinical treatment).

Refresh Interlocks

Figure 4:
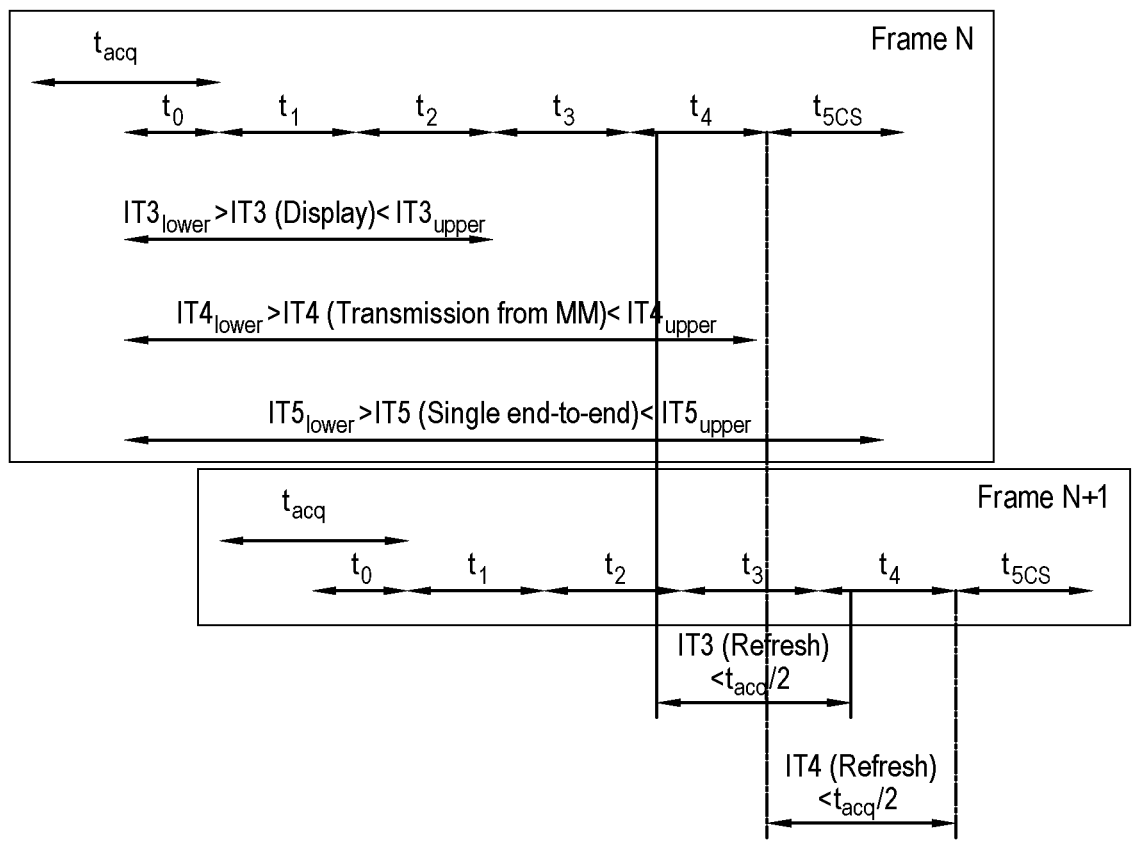
FIG. 4 is a representation of two consecutive MR-gated radiotherapy processes.

FIG. 4 is a representation of two consecutive MR-gated radiotherapy processes. The first process (labelled as 'Frame N' in FIG. 4) comprises steps including: a k-space acquisition (over a period of $t_{acq}$ ($2t_0$)), followed by: reconstruction of the k-space into a 2D (in this case) MR image (over a period of $t_1$), preparation for transmission of the 2D image by the MR sub-system to a motion manager of the linac's control system (over a period of $t_2$), transmission of the image to the motion manager (over a period of $t_3$), making a gating decision based on the received image (over a period of $t_4$), and a radiation response time (in this case over a time $t_{5CS}$ corresponding to a response time of the linac to a command a change to the pulsing state of the electron gun (106) based on an instruction received from the Motion Manager).

A second process (labelled as 'Frame N+1' in FIG. 4) respectively comprises steps including: a second k-space acquisition (during $t_{acq}$), a second reconstruction (during $t_1$), preparation for transmission of the second image to the motion manager (during of $t_2$), transmission of the second image to the motion manager (during $t_3$), making a gating decision based on the received second image (during $t_4$), and a second radiation response time (during $t_{5CS}$).

The first and second process (Frame N and Frame N+1) are consecutive in that they relate to consecutive k-space samplings wherein each k-space sampling includes a sampling of a centre of k-space. Consequently, reconstructions of those two consecutive k-space samplings result in two MR images showing an anatomy of a patient located within the field of view of the linac at two temporally adjacent time points. Those images may then be displayed on a display as adjacent frames in a cine clip. As shown in FIG. 4, the first and second processes may partially temporally overlap.

When a time point in a first of the processes (e.g. the end of duration to in frame N) is compared to a corresponding second time point in a second of the processes (e.g. the end of duration $t_4$ in frame N+1), an evaluation of the elapsed time between the first and second time points can be performed to determine whether or not the elapsed time (labelled IT4 (Refresh) in FIG. 4) corresponds to an expected temporal behaviour of the system. If that elapsed time falls outside a predetermined range, then the system is not performing as expected and an interlock may be implemented.

Although the above has been described with reference to elapsed time IT4 (Refresh) of FIG. 4, the same approach may be applied to any pair of corresponding time points in the two consecutive processes. As an example, FIG. 4 also shows an example elapsed time IT3 (Refresh) which measures the time between the end of duration $t_3$ plus a predetermined delay for Frame N and the end of duration $t_3$ plus that predetermined delay for Frame N+1. In the IT4 (Refresh) and IT3 (refresh) interlock examples of FIG. 4, example predetermined ranges of less than $t_{acq}/2$ have been given, but other ranges may instead be employed. As one possibility a predetermined range may have a non-zero positive value in order to implement an interlock in case the second process is a duplicate of the first (i.e. Frame N+1=Frame N).

Example time points between with the elapsed time may be determined include an acquisition time e.g. the middle of duration (t of FIG. 2) or the end of the acquisition during $t_{acq}$ or any of: a reconstruction time e.g. the end of reconstruction $t_1$, an end of preparation for transmission of an image to the motion manager time $t_2$, a receipt by the control system time e.g. the end of transmission of an image to the motion manager $t_3$, a gating decision time e.g. the end of making a gating decision based on a received image $t_4$, and a radiotherapy delivery time e.g. a radiation response time $t_{5CS}$, a response time to turn off the radiation beam, or a response time to turn on the radiation beam Each time point may be represented by respective time information indicating that time point.

Figure 5:
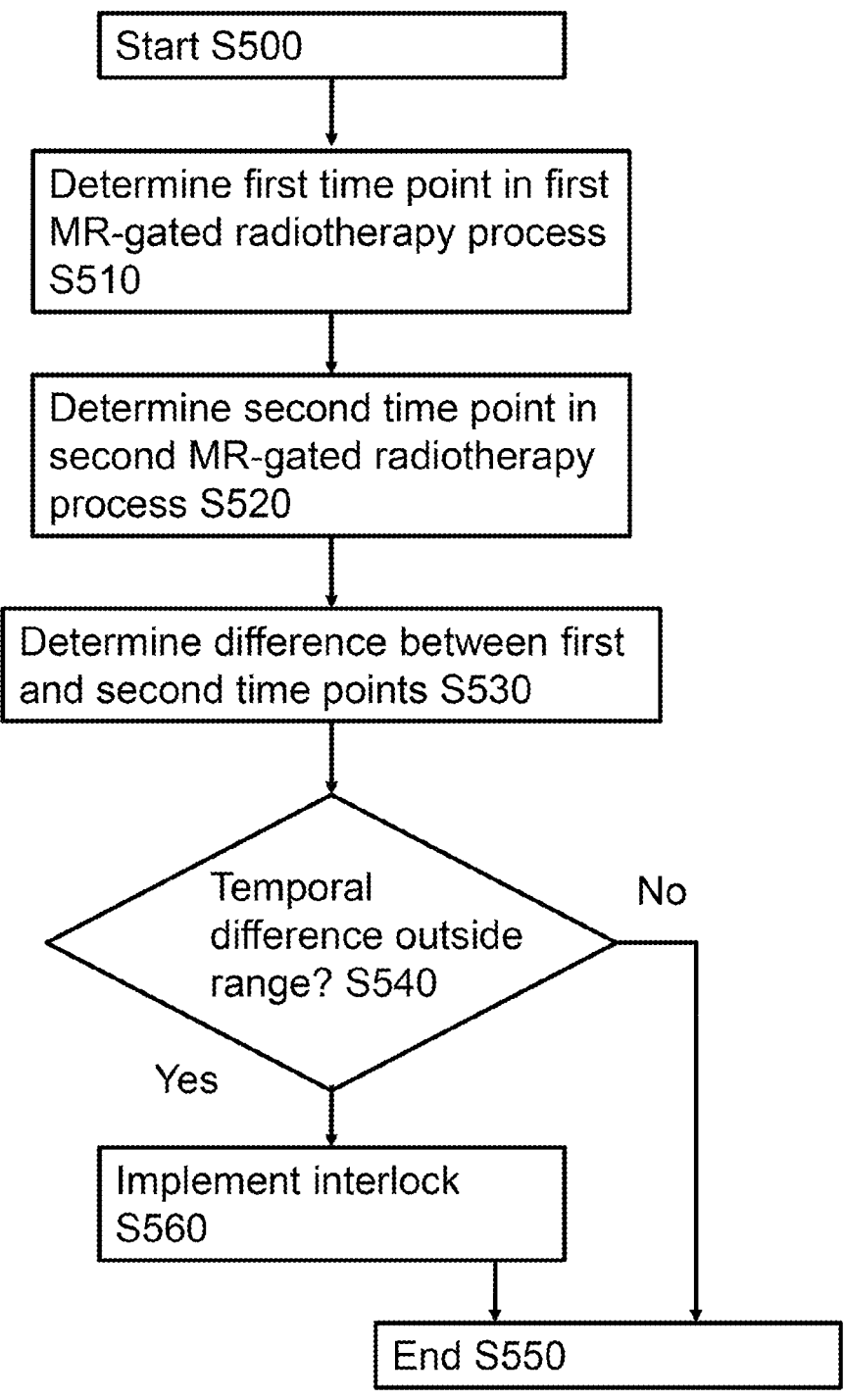
FIG. 5 is a flow diagram for a process for implementing an interlock.

FIG. 5 is a flow diagram for a process (starting at step S500) for implementing an interlock which may be performed at a control system of a Linear Accelerator (linac) arranged to perform MR-gated radiotherapy processes, each process comprising receiving a reconstructed MR image of a patient located within a field of delivery of the linac.

At step S510 first time information indicating a first time point in a first of the MR-gated radiotherapy processes is determined. At step S520 second time information indicating a second time point in a second (and consecutive) of the MR-gated radiotherapy processes is determined wherein the second time point occurred at a point within the second process that corresponds to a point within the first process at which the first time point occurred.

At step S530 a determination is made from the first and second time information of a temporal difference between the first and second time points. The determined temporal difference is then assessed at step S540 to see whether it lies outside a predetermined range of acceptable values. The predetermined range may be bounded by a single threshold demarking values on one side of which lie within the predetermined range and on the other side of which do not. The threshold itself may or may not be included within the predetermined range.

If the temporal difference does not lie outside the predetermined range then the method stops at step S550. If the temporal difference lies outside the predetermined range, then at step S560 an interlock is implemented. As one possibility, the interlock may be arranged to implement an interlock to prevent one or more actions from being taken such as preventing irradiation of the patient—for example by stopping ongoing radiation or preventing an initiation of radiation—thereby preventing patient irradiation in situations where it is determined that the system is not operating as expected. This may be achieved by disabling the electron gun 106—for example by sending a signal to cause the placement of an opaque material between the electron gun 106 and the patient or by ceasing provision of a 'fire gun' signal to the electron gun. As an additional or alternative possibility, the interlock may be arranged to prevent display on a monitor associated with the MR-linac of an image based on the patient monitoring data—such as an MR image of the patient in the field of delivery as acquired during the first process (Frame N) and/or an image acquired during the second process (Frame N+1). By blocking the display of such an image when it is determined that the system is not operating as expected, operators and clinicians are prevented from making decisions which could be erroneous. As another possibility, the interlock may cause display of an error or warning message alongside an MR image of the patient in the field of delivery as acquired during the first process (Frame N) and/or an image acquired during the second process (Frame N+1). As one possibility, an interlock counter may be implemented which counts the number of times that an interlock has been implemented during a given period (such as a patient treatment session, a day, week, month or year) and, whilst that count is below a predetermined threshold, the control system implements each interlock by blocking the display of a respective associated image and, once that predetermined threshold is reached, the control system implements each interlock by both blocking the display of a respective associated image and stopping ongoing radiation or preventing an initiation of radiation.

Although the above has been described with reference to two processes each comprising respective elements $t_{acq}$, $t_1$, $t_2$, $t_3$, $t_4$ and $t_{5CS}$, it will be appreciated that not all of those steps need be present in order to implement the described process. Furthermore, as an interlock may be implemented at an early stage of the second process (thereby preventing subsequent steps in the second process from occurring), the second process need not include all of the steps of the first process.

The above described approaches for determining time differences between consecutive processes may be combined with the above described approaches for synchronizing the clock of the control system with the clock of the MR system. For example, synchronization may occur by way of a Time Sync Server (not shown) of the MR-linac or may be performed directly between the control system and the MR system.

Intra-Frame Interlock

Figure 6:
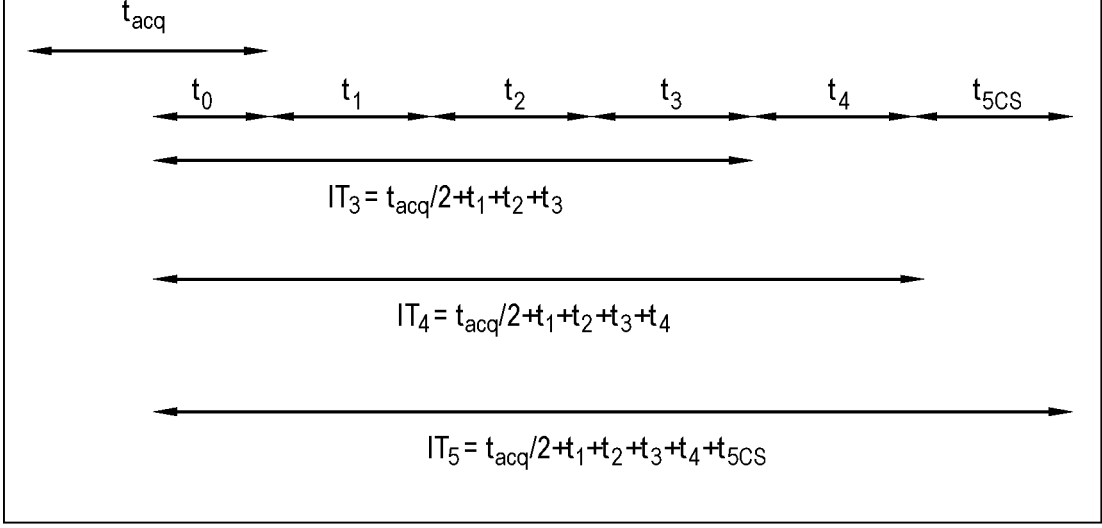
FIG. 6 is a representation of a single frame of an MR-gated radiotherapy processes.

FIG. 6 is a representation of a single frame of an MR-gated radiotherapy process that comprises steps including: a k-space acquisition (over a period of $t_{acq}$ ($2t_0$)), followed by: reconstruction of the k-space into a 2D (in this case) MR image (over a period of $t_1$), preparation for transmission of the 2D image by the MR sub-system to a motion manager of the linac's control system (over a period of $t_2$), transmission of the image to the motion manager (over a period of $t_3$), making a gating decision based on the received image (over a period of $t_4$), and a radiation response time (in this case over a time $t_{5CS}$ corresponding to a response time of the linac to a command a change to the pulsing state of the electron gun (106) based on an instruction received from the Motion Manager, as another possibility a time to provision of such a command may be employed).

When a time point of the processes (e.g. the end of duration ta) of a frame is compared to a time point of the k-space acquisition for that frame, an evaluation of the elapsed time (or latency) between the two time points can be performed to determine whether or not the elapsed time corresponds to an expected behaviour of the system. If that elapsed time falls outside a predetermined range, then the system is not performing as expected and an interlock may be implemented.

Example time points for which the elapsed time may be determined include that between the acquisition time e.g. the middle of duration $t_{acq}$ ($t_{k0}$ of FIG. 2) or the end of the acquisition during $t_{acq}$ and any of: a reconstruction time e.g. the end of reconstruction $t_1$, an end of preparation for transmission of an image to the motion manager time $t_2$, a receipt by the control system time e.g. the end of transmission of an image to the motion manager $t_3$, a gating decision time e.g. the end of making a gating decision based on a received image $t_4$, and a radiotherapy delivery time e.g. a radiation response time $t_{5CS}$, a response time to turn off the radiation beam, a response time to turn on the radiation beam, or a time to provide a command to turn on the radiation beam. Each time point may be represented by respective time information indicating that time point.

FIG. 6 also shows a number of time points about which the described approach may be based. For example an assessment of latency at the end of transmission of an image to the motion manager may be assessed with $IT3=t_{acq}/2+t_1+t_2+t_3$ being the expected elapsed time for that action to occur after the middle of duration $t_{acq}$ ($t_{k0}$ of FIG. 2) and a range (which may or may not be centred on IT3) may be defined about that expected elapsed time. Similarly, an assessment of latency at the end of making a gating decision may be assessed with $IT4=t_{acq}/2+t_1+t_2+t_3+t_4$ being the expected elapsed time for that action to occur after the middle of duration $t_{acq}$ ($t_{k0}$ of FIG. 2) and a range (which may or may not be centred on IT4) may be defined about that expected elapsed time. Likewise, an assessment of latency of a radiotherapy delivery time may be assessed with $IT5=t_{acq}/2+t_1+t_2+t_3+t_4+t_{5CS}$ being the expected elapsed time for that action to occur after the middle of duration $t_{acq}$ ($t_{k0}$ of FIG. 2) and a range (which may or may not be centred on IT5) may be defined about that expected elapsed time.

Figure 7:
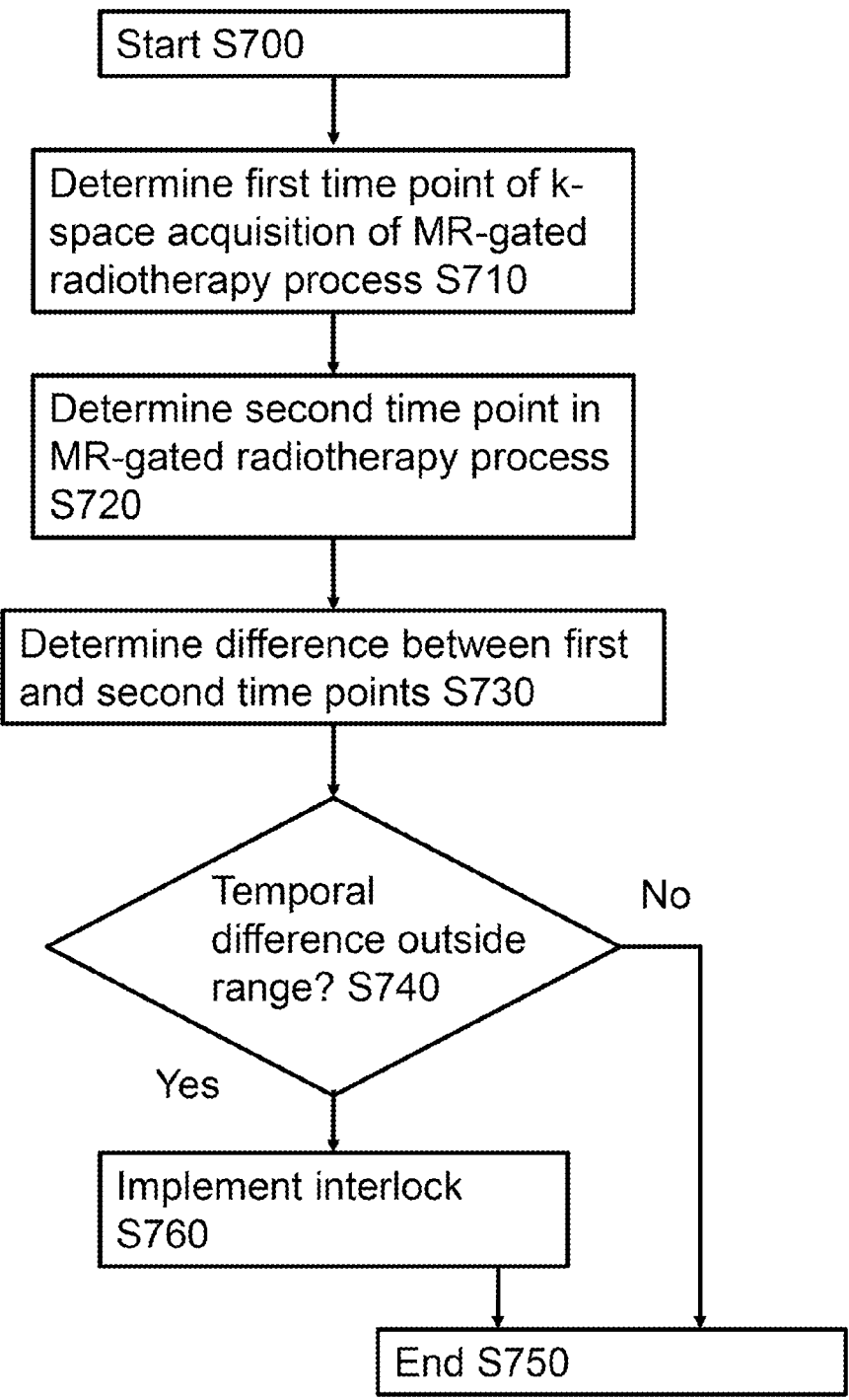
FIG. 7 is a flow diagram for a process for implementing an interlock.

FIG. 7 is a flow diagram for a process (starting at step S700) for implementing an interlock which may be performed at a control system of a Linear Accelerator (linac) arranged to perform MR-gated radiotherapy process.

At step S710 first time information indicating a first time point of a k-space acquisition for an MR image of a patient located within a field of delivery of the linac is determined. At step S720 second time information indicating a second time point of the MR-gated radiotherapy processes is determined wherein the second time point occurred at a point within the radiotherapy process subsequent to the first time point.

At step S730 a determination is made from the first and second time information of a temporal difference between the first and second time points. The determined temporal difference is then assessed at step S740 to see whether it lies outside a predetermined range of acceptable values. The predetermined range may be bounded by a single threshold demarking values on one side of which lie within the predetermined range and on the other side of which do not. The threshold itself may or may not be included within the predetermined range.

If the temporal difference does not lie outside the predetermined range then the method stops at step S750. If the temporal difference lies outside the predetermined range, then at step S760 an interlock is implemented. As one possibility, the interlock may be arranged to implement an interlock to prevent one or more actions from being taken such as preventing irradiation of the patient—for example by stopping ongoing radiation or preventing an initiation of radiation—thereby preventing patient irradiation in situations where it is determined that the system is not operating as expected. This may be achieved by disabling the electron gun 106—for example by sending a signal to cause the placement of an opaque material between the electron gun 106 and the patient or by ceasing provision of a 'fire gun' signal to the electron gun. As an additional or alternative possibility, the interlock may be arranged to prevent display on a monitor associated with the MR-linac of an image based on the patient monitoring data—such as an MR image of the patient in the field of delivery as acquired during the process. By blocking the display of such an image when it is determined that the system is not operating as expected, operators and clinicians are prevented from making decisions which could be erroneous.

FIG. 4 also shows a number of examples of possible predetermined ranges for interlocks. In particular A range for assessing latency at the end of transmission of an image to the motion manager may be defined as IT3 (Display) having respective lower and upper limits of $IT3_{lower}$ and $IT3_{upper}$. Similarly, a range for assessing latency at the end of making a gating decision may be assessed with defined as IT4 (Transmission from MM) having respective lower and upper limits of $IT4_{lower}$ and $IT4_{upper}$. Likewise, a range for assessing latency of a radiotherapy delivery time may be defined as IT5 (Single end-to-end) having respective lower and upper limits of $IT5_{lower}$ and $IT5_{upper}$.

The above described approaches for determining time differences between time points within a frame may be combined with the above described approaches for synchronizing the clock of the control system with the clock of the MR system. For example, synchronization may occur by way of a Time Sync Server (not shown) of the MR-linac or may be performed directly between the control system and the MR system.

Computer Implementation

Figure 8:
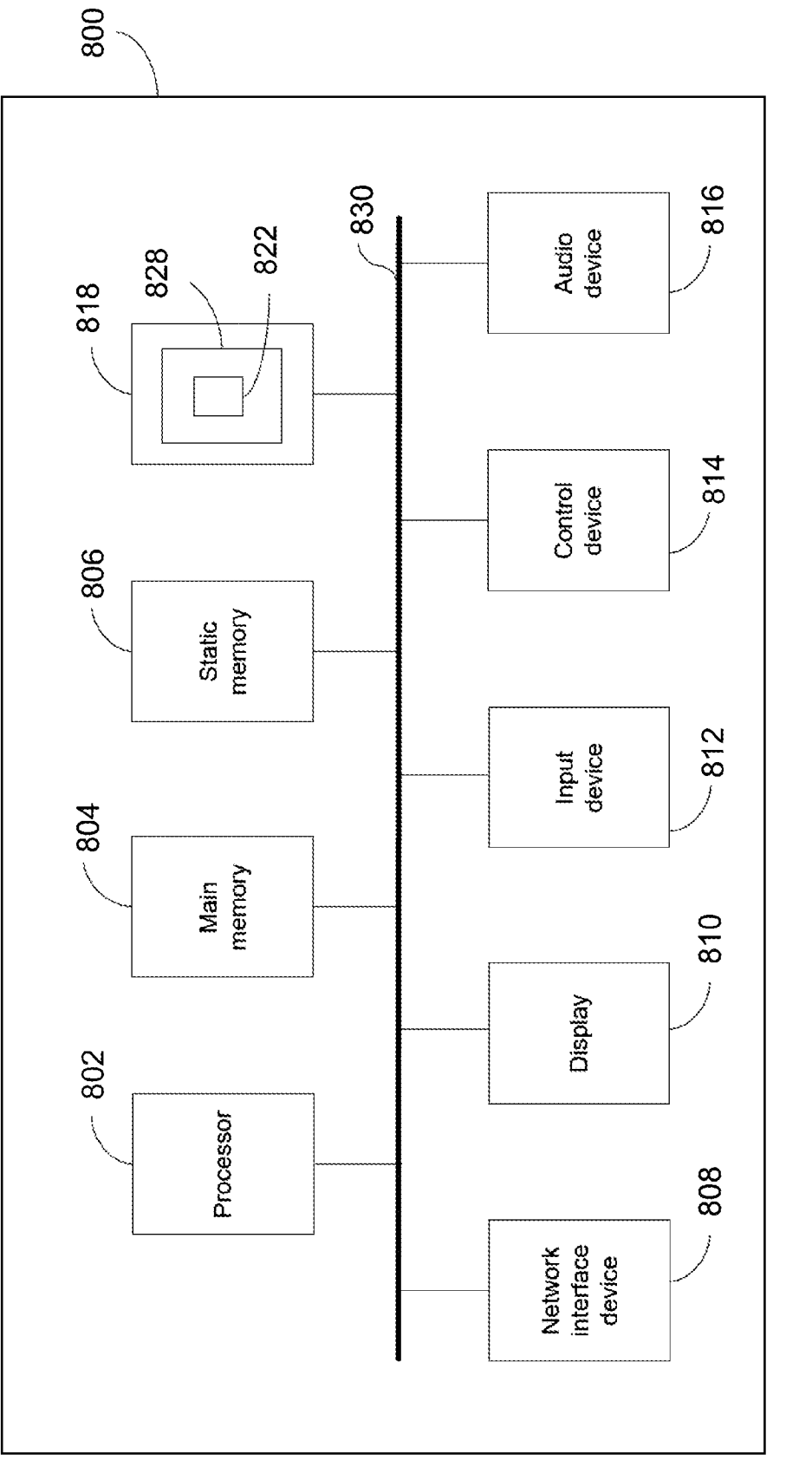
FIG. 8 shows an example implementation of a computing device according to the present disclosure.

FIG. 8 illustrates a block diagram of one implementation of a computing device 800 within which a set of instructions, for causing the computing device to perform any one or more of the methodologies discussed herein, may be executed so as to thereby embody the control system. In alternative implementations, the computing device may be connected (e.g., networked) to other machines in a Local Area Network (LAN), an intranet, an extranet, or the Internet. The computing device may operate in the capacity of a server or a client machine in a client-server network environment, or as a peer machine in a peer-to-peer (or distributed) network environment. The computing device may be a personal computer (PC), a tablet computer, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, while only a single computing device is illustrated, the term "computing device" shall also be taken to include any collection of machines (e.g., computers) that individually or jointly execute a set (or multiple sets) of instructions to perform any one or more of the methodologies discussed herein. The computing device 800 may correspond to the control system, controller or control device as described herein.

The example computing device 800 includes a processing device 802, a main memory 804 (e.g., read-only memory (ROM), flash memory, dynamic random access memory (DRAM) such as synchronous DRAM (SDRAM) or Rambus DRAM (RDRAM), etc.), a static memory 806 (e.g., flash memory, static random access memory (SRAM), etc.), and a secondary memory (e.g., a data storage device 818), which communicate with each other via a bus 830.

Processing device 802 represents one or more general-purpose processors such as a microprocessor, central processing unit, or the like. More particularly, the processing device 802 may be a complex instruction set computing (CISC) microprocessor, reduced instruction set computing (RISC) microprocessor, very long instruction word (VLIVV) microprocessor, processor implementing other instruction sets, or processors implementing a combination of instruction sets. Processing device 802 may also be one or more special-purpose processing devices such as an application specific integrated circuit (ASIC), a field programmable gate array (FPGA), a digital signal processor (DSP), network processor, or the like. Processing device 802 is configured to execute the processing logic (instructions 822) for performing the operations and steps discussed herein.

The computing device 800 may further include a network interface device 808. The computing device 800 also may include a video display unit 810 (e.g., a liquid crystal display (LCD) or a cathode ray tube (CRT)), an alphanumeric input device 812 (e.g., a keyboard or touchscreen), a cursor control device 814 (e.g., a mouse or touchscreen), and an audio device 816 (e.g., a speaker).

The data storage device 818 may include one or more machine-readable storage media (or more specifically one or more non-transitory computer-readable storage media) 828 on which is stored one or more sets of instructions 822 embodying any one or more of the methodologies or functions described herein. The instructions 822 may also reside, completely or at least partially, within the main memory 804 and/or within the processing device 802 during execution thereof by the computer system 800, the main memory 804 and the processing device 802 also constituting computer-readable storage media.

The various methods described above may be implemented by a computer program. The computer program may include computer code arranged to instruct a computer to perform the functions of one or more of the various methods described above. The computer program and/or the code for performing such methods may be provided to an apparatus, such as a computer, on one or more computer readable media or, more generally, a computer program product. The computer readable media may be transitory or non-transitory. The one or more computer readable media could be, for example, an electronic, magnetic, optical, electromagnetic, infrared, or semiconductor system, or a propagation medium for data transmission, for example for downloading the code over the Internet. Alternatively, the one or more computer readable media could take the form of one or more physical computer readable media such as semiconductor or solid state memory, magnetic tape, a removable computer diskette, a random access memory (RAM), a read-only memory (ROM), a rigid magnetic disc, and an optical disk, such as a CD-ROM, CD-R/W or DVD.

In an implementation, the modules, components and other features described herein can be implemented as discrete components or integrated in the functionality of hardware components such as ASICS, FPGAs, DSPs or similar devices.

A "hardware component" is a tangible (e.g., non-transitory) physical component (e.g., a set of one or more processors) capable of performing certain operations and may be configured or arranged in a certain physical manner. A hardware component may include dedicated circuitry or logic that is permanently configured to perform certain operations. A hardware component may be or include a special-purpose processor, such as a field programmable gate array (FPGA) or an ASIC. A hardware component may also include programmable logic or circuitry that is temporarily configured by software to perform certain operations.

Accordingly, the phrase "hardware component" should be understood to encompass a tangible entity that may be physically constructed, permanently configured (e.g., hard-wired), or temporarily configured (e.g., programmed) to operate in a certain manner or to perform certain operations described herein.

In addition, the modules and components can be implemented as firmware or functional circuitry within hardware devices. Further, the modules and components can be implemented in any combination of hardware devices and software components, or only in software (e.g., code stored or otherwise embodied in a machine-readable medium or in a transmission medium).

Unless specifically stated otherwise, as apparent from the following discussion, it is appreciated that throughout the description, discussions utilizing terms such as "receiving", "determining", "comparing", "enabling", "maintaining," "identifying," "applying," "transmitting," "generating," or the like, refer to the actions and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The approaches described herein may be embodied on a computer-readable medium, which may be a non-transitory computer-readable medium. The computer-readable medium may carry computer-readable instructions arranged for execution upon a processor so as to cause the processor to carry out any or all of the methods described herein.

The term "computer-readable medium" as used herein refers to any medium that stores data and/or instructions for causing a processor to operate in a specific manner. Such storage medium may comprise non-volatile media and/or volatile media. Non-volatile media may include, for example, optical or magnetic disks. Volatile media may include dynamic memory. Exemplary forms of storage medium include, a floppy disk, a flexible disk, a hard disk, a solid state drive, a magnetic tape, or any other magnetic data storage medium, a CD-ROM, any other optical data storage medium, any physical medium with one or more patterns of holes, a RAM, a PROM, an EPROM, a FLASH-EPROM, NVRAM, and any other memory chip or cartridge.

There is described herein timing-based methods, systems, and computer readable mediums for a gated linear accelerator include synchronizing a local clock of the linear accelerator with a clock of a patient monitoring system, determining latencies within one or more MR-gated radiotherapy processes and implementing latency based interlocks.

It is to be understood that the above description is intended to be illustrative, and not restrictive. Many other implementations will be apparent to those of skill in the art upon reading and understanding the above description. Although the present disclosure has been described with reference to specific example implementations, it will be recognized that the disclosure is not limited to the implementations described, but can be practiced with modification and alteration within the scope of the appended claims. Accordingly, the specification and drawings are to be regarded in an illustrative sense rather than a restrictive sense. The scope of the disclosure should, therefore, be determined with reference to the appended claims, along with the full scope of equivalents to which such claims are entitled.

Examples are set out in the following list of numbered clauses:

1. A method performed at a control system of a gated Linear Accelerator (linac), the control system having a control clock, the method comprising:
   synchronizing the control clock with a monitoring clock of a patient monitoring system;
   receiving from the patient monitoring system and for a patient located within a field of delivery of the linac:
      patient monitoring data for use in gating radiation delivery to the patient, and
      an acquisition time of the patient monitoring data according to the monitoring clock;
   comparing the acquisition time with a time of the control clock to determine a latency of the patient monitoring data.

2. The method of clause 1, wherein the patient monitoring system is a Magnetic Resonance (MR) machine and the patient monitoring information is an MR data of the patient located within a field of delivery of the linac.

3. The method of clause 2, wherein the MR data comprises k-space data of the patient located within a field of delivery of the linac.

4. The method of clause 2 or 3, wherein the MR data comprises a reconstructed MR image of the patient located within a field of delivery of the linac.

5. The method of any preceding clause, further comprising:
   determining that the latency lies outside a predetermined range; and
   implementing an interlock to prevent one or more actions from being taken.

6. The method of clause 5, wherein the implemented interlock prevents irradiation of the patient.

7. The method of clause 5 or 6, wherein the implemented interlock prevents display of the MR image.

8. The method of any of any preceding clause, wherein the predetermined range is bounded by a single threshold.

9. A control system for a gated Linear Accelerator (linac), the control system having a control clock and being arranged to:
   synchronize the control clock with a monitoring clock of a patient monitoring system;
   receive from the patient monitoring system and for a patient located within a field of delivery of the linac:
      patient monitoring data for use in gating radiation delivery to the patient, and
      an acquisition time of the patient monitoring data according to the monitoring clock;
   compare the acquisition time with a time of the control clock to determine a latency of the patient monitoring data.

10. The control system of clause 9, wherein the patient monitoring system is a Magnetic Resonance (MR) machine and the patient monitoring information is an MR data of the patient located within a field of delivery of the linac.

11. The control system of clause 10, wherein the MR data comprises k-space data of the patient located within a field of delivery of the linac.

12. The control system of clause 10 or 11, wherein the MR data comprises a reconstructed MR image of the patient located within a field of delivery of the linac.

13. The control system of any of clauses 9 to 12, the control system being further arranged to:
   determine that the latency lies outside a predetermined range; and
   implement an interlock to prevent one or more actions from being taken.

14. The control system of clause 13, wherein the implemented interlock prevents irradiation of the patient.

15. The control system of clause 13 or 14, wherein the implemented interlock prevents display of the MR image.

16. The control system of any of clauses 9 to 15, wherein the predetermined range is bounded by a single threshold.

17. A computer-readable medium containing instructions which, when executed by a processor, cause the processor to perform the method of any of clauses 1 to 8.

18. A method performed at a control system of a Linear Accelerator (linac) arranged to perform Magnetic Resonance (MR)-gated radiotherapy processes, each process comprising receiving a reconstructed MR image of a patient located within a field of delivery of the linac, the method comprising:
   determining first time information indicating a first time point in a first of the MR-gated radiotherapy processes;
   determining second time information indicating a second time point in a second of the MR-gated radiotherapy processes, wherein the first and second of the MR-gated radiotherapy processes are consecutive processes and the second time point occurred at a point in the second MR-gated radiotherapy process that corresponds to the point in the first MR-gated radiotherapy process at which the first time point occurred; and
   determining from the first and second time information that a temporal difference between the first and second time points lies outside a predetermined range; and
   implementing an interlock.

19. The method of clause 18, wherein the implemented interlock prevents irradiation of the patient.

20. The method of clause 18 or 19, wherein the implemented interlock prevents display of an MR image or images of the first and/or second MR-gated radiotherapy process.

21. The method of any of clauses 18 to 20, wherein the first and second time points are acquisition times of first and second MR images of the respective first and second MR-gated radiotherapy processes.

22. The method of any of clauses 18 to 20, wherein the first and second time points are reconstruction times of first and second MR images of the respective first and second MR-gated radiotherapy processes.

23. The method of any of clauses 18 to 20, wherein the first and second time points are receipt by the control system times of reconstructed first and second MR images of the respective first and second MR-gated radiotherapy processes.

24. The method of any of clauses 18 to 20, wherein each process comprises analysing the reconstructed MR image to make a gating decision.

25. The method of clause 24, wherein the first and second time points are gating decision times of the first and second MR-gated radiotherapy processes.

26. The method of any of clauses 18 to 20, wherein each process comprises instructing delivery of radiotherapy to the patient.

27. The method of clause 26, wherein the first and second time points are radiotherapy delivery times of the first and second MR-gated radiotherapy processes.

28. The method of any of clauses 18 to 27, wherein each process comprises, when the gating decision is to irradiate the patient, and no interlock prevents irradiation, irradiating the patient.

29. The method of any of clauses 18 to 28, wherein the predetermined range is bounded by a single threshold.

30. The method of any of clauses 18 to 29, further comprising synchronizing a control clock of the control system with a monitoring clock of a patient monitoring system from which the reconstructed MR image of each process is received.

31. A control system for a Linear Accelerator (linac) arranged to perform Magnetic Resonance (MR)-gated radiotherapy processes, each process comprising receiving a reconstructed MR image of a patient located within a field of delivery of the linac, the control system being arranged to:

determine first time information indicating a first time point in a first of the MR-gated radiotherapy processes;

determine second time information indicating a second time point in a second of the MR-gated radiotherapy processes, wherein the first and second of the MR-gated radiotherapy processes are consecutive processes and the second time point occurred at a point in the second MR-gated radiotherapy process that corresponds to the point in the first MR-gated radiotherapy process at which the first time point occurred; and determine from the first and second time information that a temporal difference between the first and second time points lies outside a predetermined range; and implement an interlock.

32. The control system of clause 31, wherein the implemented interlock prevents irradiation of the patient.

33. The control system of clause 31 or 32, wherein the implemented interlock prevents display of an MR image or images of the first and/or second MR-gated radiotherapy process.

34. The control system of any of clauses 31 to 33, wherein the first and second time points are acquisition times of first and second MR images of the respective first and second MR-gated radiotherapy processes.

35. The control system of any of clauses 31 to 33, wherein the first and second time points are reconstruction times of first and second MR images of the respective first and second MR-gated radiotherapy processes.

36. The control system of any of clauses 31 to 33, wherein the first and second time points are receipt by the control system times of reconstructed first and second MR images of the respective first and second MR-gated radiotherapy processes.

37. The control system of any of clauses 31 to 33, wherein each process comprises analysing the reconstructed MR image to make a gating decision.

38. The control system of clause 37, wherein the first and second time points are gating decision times of the first and second MR-gated radiotherapy processes.

39. The control system of any of clauses 31 to 33, wherein each process comprises instructing delivery of radiotherapy to the patient.

40. The control system of clause 39, wherein the first and second time points are radiotherapy delivery times of the first and second MR-gated radiotherapy processes.

41. The control system of any of clauses 31 to 40, wherein each process comprises, when the gating decision is to irradiate the patient, and no interlock prevents irradiation, irradiating the patient.

42. The control system of any of clauses 31 to 41, wherein the predetermined range is bounded by a single threshold.

43. The control system of any of clauses 31 to 42, the control system being further arranged to synchronize a control clock of the control system with a monitoring clock of a patient monitoring system from which the reconstructed MR image of each process is received.

44. A computer-readable medium containing instructions which, when executed by a processor, cause the processor to perform the method of any of clauses 18 to 30.

45. A method performed at control system of a Magnetic Resonance (MR)-gated Linear Accelerator (linac), the method comprising:

determining first time information indicating a first time point of a k-space acquisition for an MR image of a patient located within a field of delivery of the linac;

determining second time information indicating a second time point, wherein the second time point is subsequent to the first time point and occurs during an MR-gated procedure for providing the patient with radiotherapy;

determining from the first and second time information that a temporal difference between the first and second time points lies outside a predetermined range; and implementing an interlock to prevent one or more actions from being taken.

46. The method of clause 45, wherein the implemented interlock prevents irradiation of the patient.

47. The method of clause 45 or 46, wherein the implemented interlock prevents display of the MR image.

48. The method of any of clauses 45 to 47, wherein the second time point is a time of receipt of the MR image by the control system.

49. The method of any of clauses 45 to 47, wherein the second time point is a time of a gating decision that has been made based on the MR image.

50. The method of any of clauses 45 to 47, wherein the second time point is a time of radiotherapy delivery by the linac.

51. The method of any of clauses 45 to 50, wherein the predetermined range is bounded by a single threshold.

52. The method of any of clauses 45 to 51, further comprising synchronizing a control clock of the control system with a monitoring clock of a system that performed the k-space acquisition.

53. A control system for a Magnetic Resonance (MR)-gated Linear Accelerator (linac), the control system being arranged to:

determine first time information indicating a first time point of a k-space acquisition for an MR image of a patient located within a field of delivery of the linac;

determine second time information indicating a second time point, wherein the second time point is subsequent to the first time point and occurs during an MR-gated procedure for providing the patient with radiotherapy;

determine from the first and second time information that a temporal difference between the first and second time points lies outside a predetermined range; and implement an interlock to prevent one or more actions from being taken.

54. The control system of clause 53, wherein the implemented interlock prevents irradiation of the patient.

55. The control system of clause 53 or 54, wherein the implemented interlock prevents display of the MR image.

56. The control system of any of clauses 53 to 55, wherein the second time point is a time of receipt of the MR image by the control system.

57. The control system of any of clauses 53 to 55, wherein the second time point is a time of a gating decision that has been made based on the MR image.

58. The control system of any of clauses 53 to 55, wherein the second time point is a time of radiotherapy delivery by the linac.

59. The control system of any of clauses 53 to 58, wherein the predetermined range is bounded by a single threshold.

60. The control system of any of clauses 53 to 59, the control system being further arranged to synchronize a control clock of the control system with a monitoring clock of a system that performed the k-space acquisition.

61. A computer-readable medium containing instructions which, when executed by a processor, cause the processor to perform the method of any of clauses 45 to 52.

What is claimed is:

1. A method performed at a control system of a gated Linear Accelerator (linac), the control system having a control clock, the method comprising:

synchronizing the control clock with a monitoring clock of a patient monitoring system;

receiving from the patient monitoring system and for a patient located within a field of delivery of the linac:

patient monitoring data for use in gating radiation delivery to the patient; and an acquisition time of the patient monitoring data according to the monitoring clock;

comparing the acquisition time with a time of the control clock to determine a latency of the patient monitoring data;

determining whether the latency lies outside a predetermined range; and responsive to determining that the latency lies outside the predetermined range, implementing an interlock to prevent one or more actions from being taken.

2. The method of claim 1, wherein the patient monitoring system includes a Magnetic Resonance (MR) machine, and wherein the patient monitoring data includes an MR data of the patient located within a field of delivery of the linac.

3. The method of claim 2, wherein the MR data comprises k-space data of the patient located within a field of delivery of the linac.

4. The method of claim 2, wherein the MR data comprises a reconstructed MR image of the patient located within a field of delivery of the linac.

5. The method of claim 1, wherein the implemented interlock prevents irradiation of the patient.

6. The method of claim 4, wherein the implemented interlock prevents display of the reconstructed MR image.

7. The method of claim 1, wherein the predetermined range is bounded by a single threshold.

8. A control system for a gated Linear Accelerator (linac), the control system having a control clock and being arranged to:

synchronize the control clock with a monitoring clock of a patient monitoring system;

receive from the patient monitoring system and for a patient located within a field of delivery of the linac:

patient monitoring data for use in gating radiation delivery to the patient, and an acquisition time of the patient monitoring data according to the monitoring clock; and compare the acquisition time with a time of the control clock to determine a latency of the patient monitoring data;

determine whether the latency lies outside a predetermined range; and responsive to determining that the latency lies outside the predetermined range, implement an interlock to prevent one or more actions from being taken.

9. The control system of claim 8, wherein the patient monitoring system includes a Magnetic Resonance (MR) machine, and wherein the patient monitoring data is an MR data of the patient located within a field of delivery of the linac.

10. The control system of claim 9, wherein the MR data comprises k-space data of the patient located within a field of delivery of the linac.

11. The control system of claim 9, wherein the MR data comprises a reconstructed MR image of the patient located within a field of delivery of the linac.

12. The control system of claim 8, wherein the implemented interlock prevents irradiation of the patient.

13. The control system of claim 11, wherein the implemented interlock prevents display of the reconstructed MR image.

14. The control system of claim 8, wherein the predetermined range is bounded by a single threshold.

15. A non-transitory computer-readable medium containing instructions which, when executed by a processor, cause the processor to:

synchronize a control clock with a monitoring clock of a patient monitoring system;

receive from the patient monitoring system and for a patient located within a field of delivery of a gated linear accelerator:

patient monitoring data for use in gating radiation delivery to the patient; and an acquisition time of the patient monitoring data according to the monitoring clock;

compare the acquisition time with a time of the control clock to determine a latency of the patient monitoring data;

determine whether the latency lies outside a predetermined range; and responsive to determining that the latency lies outside the predetermined range, implement an interlock to prevent one or more actions from being taken.

16. The non-transitory computer-readable medium of claim 15, wherein the implemented interlock prevents irradiation of the patient, and wherein the predetermined range is bounded by a single threshold.

17. The non-transitory computer-readable medium of claim 16, wherein the patient monitoring system includes a Magnetic Resonance (MR) machine, wherein the patient monitoring data includes an MR data of the patient located within a field of delivery of the gated linear accelerator, wherein the MR data comprises a reconstructed MR image of the patient located within a field of delivery of the gated linear accelerator, and wherein the implemented interlock prevents display of the reconstructed MR image.

18. The method of claim 1, wherein the predetermined range corresponds to a range of positions in a respiratory cycle of the patient to reduce or prevent dosimetric error in the delivery of radiation.

19. The control system of claim 8, wherein the predetermined range corresponds to a range of positions in a respiratory cycle of the patient to reduce or prevent dosimetric error in the delivery of radiation.

20. The non-transitory computer-readable medium of claim 15, wherein the predetermined range corresponds to a range of positions in a respiratory cycle of the patient to reduce or prevent dosimetric error in the delivery of radiation.

* * * * *